United States Patent [19]

Bodenmueller et al.

[11] Patent Number: 5,399,482
[45] Date of Patent: Mar. 21, 1995

[54] METHOD FOR THE DETECTION OF MICROMETASTASES IN MESENCHYMAL TISSUE

[75] Inventors: Heinz Bodenmueller, Tutzing; Gert Riethmueller, Munich, both of Germany

[73] Assignee: Boehringer Mannheim GmbH, Mannheim, Germany

[21] Appl. No.: 32,050

[22] Filed: Mar. 16, 1993

[30] Foreign Application Priority Data

Mar. 16, 1992 [DE] Germany .................. 42 08 422.9

[51] Int. Cl.$^6$ .............. G01N 33/574; G01N 33/53; G01N 33/543
[52] U.S. Cl. ................ 435/7.23; 435/7.24; 435/7.92; 436/63; 436/64; 436/813
[58] Field of Search ............. 435/7.23, 7.24, 7.92; 436/63, 64, 813

[56] References Cited

U.S. PATENT DOCUMENTS 4,294,284 10/1981 Jones et al. .................. 424/101
5,168,044 12/1992 Joyce et al. .................. 435/7.24

FOREIGN PATENT DOCUMENTS 0267355   3/1987  European Pat. Off. .
0267355B1 5/1988  European Pat. Off. .
0449269   3/1991  European Pat. Off. .
91/10139  7/1991  WIPO .
92/0258   2/1992  WIPO .

OTHER PUBLICATIONS

Abstract of SU 1 649 444, Derwent Publications Ltd. Database WPI, Section Ch, Week 9217.
Bergmeyer, *Methods of Enzymatic Analysis*, 3rd Edition, vol. II, 1983, p. 33, table 2.
Schlimok et al., "Micrometastatic Tumor Cells in Bone Marrow of Patients with Gastric Cancer: Methodological Aspects of Detection and Prognostic Significance," *Eur J Cancer* 27(11) 1461–65 1991.
Hall et al., "Characterization of the Intermediate Filament Proteins of Murine Mammary Gland Epithelial Cells," *Experimental Cell Research*, 162; pp. 379–389, 1986.

*Primary Examiner*—Toni R. Scheiner
*Attorney, Agent, or Firm*—Nikaido, Marmelstein, Murray & Oram

[57] ABSTRACT

The present invention concerns a method for the detection of micrometastases of ectodermal or entodermal tumors. Cells from mesenchymal tissue, preferably from bone marrow, are subjected to a fractional lysis. Cytokeratins or fragments thereof are immunologically detected in the cell supernatant.

13 Claims, No Drawings

METHOD FOR THE DETECTION OF MICROMETASTASES IN MESENCHYMAL TISSUE

The invention concerns a method for the detection of micrometastases of ectodermal and entodermal tumours in mesenchymal tissue by means of fractional cell lysis in combination with a sandwich immunoassay.

The detection of micrometastases is of great importance for the prognosis of a tumour disease. A systemic dissemination of the tumour cells often already occurs before diagnosis or removal of the primary tumour. If metastatic spread can be detected early this can be treated with good chances of success for example by chemotherapy. On the other hand, superfluous follow-up treatments can be avoided after the operative removal of the primary tumour if it can be ascertained that no metastases are present.

In epithelial tumours of ectodermal or entodermal origin the detection of micrometastases by means of an increased serum level of tumour specific antigens such as for example CEA (carcinoembryonic antigen), CA 15-3, CA-19-9, CA 125, PSA (prostate-specific antigen) or cytokeratin fragments is very problematic since such antigens are also released into the serum in various inflammations of normal non-degenerate epithelial cells.

Changes in the concentration of these markers for epithelial tumours can therefore indicate the presence of tumours in an advanced stage as for example described in WO 91/10139 but not, however, the presence of micrometastases.

A method for the detection of micrometastases in bone marrow of tumour patients is described by Schlimok et al., Eur. J. Cancer, Vol. 27, 1461-1465, 1991. Individual epithelial tumour cells or small cell agglomerations of epithelial origin can be detected in the bone marrow by means of a relatively time-consuming immunocytological method. Bone marrow was collected by puncture and the mononuclear cells were prepared by density gradient centrifugation, subsequent washing and renewed centrifugation. The cells were centrifuged on glass slides and fixed there. In a further step monoclonal antibodies against specific epithelial antigens preferably cytokeratins were applied. The antibody reaction was detected by APAAP technology (Cordell et al., J. Histochem. Cytochem. 32, 219-229, 1984) using a polyvalent rabbit antiserum against mouse Ig and preformed complexes of alkaline phosphatase and monoclonal antibodies against alkaline phosphatase. Positive cells showed a cytoplasmic colouration and could be evaluated microscopically without contrast staining. This method can also be carried out with enzymatically-labelled, fluorescence-labelled or radioactively-labelled antibodies. This method seems to be too time-consuming as a routine method for the examination of a large number of patients in clinical laboratory practice.

The object of the present invention was therefore to provide a simple method for the detection of micrometastases of ectodermal or entodermal tumours.

This object is achieved by the present invention which is characterized further in the claims. The object is in particular achieved by a method for detecting micrometastases of ectodermal or entodermal origin by collecting mesenchymal tissue cells, lysing said mesenchymal tissue cells, and detecting specific ectodermal or entodermal antigens immunologically in the cells supernatant.

In addition the invention concerns a test kit for the detection of micrometastases which contains the necessary reagents for cell lysis and for the immunological detection in at least two separate package units.

It surprisingly turned out that even a few cells of ectodermal or entodermal origin can be detected in mesenchymal tissue, such as for example bone marrow or blood cells, in which these cells normally do not occur by the method according to the present invention. Thus it is even possible to detect the early stages of metastatic spread of ectodermal or entodermal tumours. These tumours are usually epithelial tumours which can be of ectodermal or entodermal origin. These include for example carcinomas such as the common mammacarcinoma, gastric carcinoma, colorectal carcinoma, tumours of the urogenital tract such as carcinoma of the bladder, kidney or prostate carcinomas or the bronchial carcinoma which is not small-celled. All markers which do not occur in mesenchymal tissue can in principle serve as tumour markers e.g. cytokeratins, mucines, hormone receptors such as EGF or oestrogen receptors, proteases such as cathepsins, tumour markers such as CEA, CA 15-3, PSA (prostate-specific antigen), CA 19-9, CA 72-4 or oncogenes such as myc, p53, ras and HER 2. Cytokeratins or cytokeratin fragments are particularly preferably used as specific antigens. As intermediary filament proteins these are components of the cytoskeleton of epithelial cells. 20 different cytokeratins are known of which cytokeratins 1 to 8 are denoted basic cytokeratins and cytokeratins 9 to 20 acidic cytokeratins. The complexity and composition of the cytokeratins differs in the various epithelial tissues i.e. epithelial cells have a cytokeratin composition which is typical for the respective tissue. Therefore it is sometimes possible to deduce the primary tumour from the respective cytokeratins detected in the mesenchymal tissue.

Intact cytokeratin molecules are integral components of the intermediary filaments of the cells and as such are poorly water-soluble. It was therefore particularly surprising that these cytokeratins or fragments thereof could be determined by a simple immunological test after a normal cell lysis without any further pretreatment of the cell supernatant. EP-B-0 267 355 expressly requires an additional step in the procedure for the immunological detection of intermediary filament proteins in order to solubilize the proteins. In this method the tissue sample is subjected to an enzymatic digestion.

Mesenchymal tissue is collected in the method according to the present invention. Bone marrow is preferably used. This is collected using a common puncture needle. A double puncture is recommended in order to increase the success rate.

It is preferred to purify the collected tissue sample before the mesenchymatic tissue cells are lysed. It is especially the aim to separate the erythrocytes from the remaining nucleated cells. This can be done for example by a density gradient centrifugation. The nucleated cells can also be bound for example to magnetic beads to which special receptors for the nucleated cells are attached. After binding of the nucleated cells to the receptors the beads are separated by conventional methods. The most preferred method is a lysis of the erythrocytes. In this case a fractional cell lysis of the mesenchymal tissue cells is carried out. Firstly the erythrocytes are treated with a lysis buffer. This buffer is preferably a buffer containing ammonium chloride. Ammonium chloride is preferably present at concentrations of 80 to 100 g/l. The pH value is 7.0 to 8.0. Further auxiliary substances such as for example complexing agents such as EDTA may also be included.

The mesenchymal cells are mixed with 10–100-fold amount of lysis buffer and incubated for several minutes, 5 minutes are usually sufficient, preferably at room temperature. Subsequently the remaining non-lysed nucleated cells are centrifuged off. The cell pellet is resuspended in buffer, preferably PBS buffer. If desired the cell count can be determined at this stage and adjusted to a certain value. This enables a more exact comparison of different samples. The nucleated cells are lysed after renewed centrifugation and resuspension, preferably in buffered physiological saline.

The lysis can be carried out by treatment with a detergent such as Nonidet P40 whereby a 30 minute incubation at room temperature is sufficient, by freezing at −20° C. or preferably by treatment with ultrasound. After renewed centrifugation in order to separate insoluble cell debris, the specific antigens of the ectodermal or entodermal cells are detected immunologically in the supernatant.

All the usual immunological methods which guarantee an adequate specificity and sensitivity can be used for the immunological detection. These are especially heterogeneous methods. Sandwich assays in which the sample is incubated with at least two receptors $R_1$ and $R_2$ which are capable of specific binding to the specific antigen to be detected, are most suitable. Receptor $R_1$ is in this case coupled to a solid phase or can be coupled to this in the course of the test procedure. Methods for this are known to a person skilled in the art, for example coupling via the binding pair biotin/avidin or streptavidin. Receptor $R_2$ contains a label for example an enzyme, a fluorescent, chemiluminescent or radioactive group.

Preferably antibodies and particularly preferably monoclonal antibodies against the tumour-specific antigens are used as receptors. In order to ensure a high specificity of the immunological test, the receptors should bind to different epitopes of the antigen if possible. Examples of such receptor pairs are known for various tumour antigens (Int. J. Cancer, 38, 47–53 (1986); T. A. Waldmann, Science, 252 1657 ff (1991); Int. J. Cancer, 3, 50–55 (1988)). WO 91/10139 describes such a receptor pair for the detection of cytokeratin 19 which seems particularly suitable for the detection of epithelial tumours. The method described therein is suitable for the detection of micrometastases in bone marrow in the method according to the present invention.

The sensitivity of the immunological method of detection should be high enough to be able to detect less than 1000 cells, preferably less than 100 cells of ectodermal or entodermal origin among $5 \times 10^6$ bone marrow leucocytes. This sensitivity is for example achieved by the enzyme immunoassay described in WO 91/10139.

If it is necessary to increase the sensitivity of an immunological test when for example the specific antigens are only present at a very low concentration, this can be achieved by using a receptor mixture. A mixture of two or more receptors (R1a, R1b, etc), which are preferably monoclonal antibodies can be used for example on the solid phase side. The receptors R1a, R1b, etc. are directed against various specific ectodermal or entodermal antigens. In the case of cytokeratins, antibodies against cytokeratin 8, 18 and 19 can for example be used simultaneously or an antibody which specifically recognizes several cytokeratins such as a monoclonal antibody which recognizes conservative epitopes of the cytokeratins. Since when micrometastases occur it would be expected that the concentration of the specific antigens in the cell supernatant would be very low and the binding capacity of the solid phase would not be exceeded by a single antigen, then if several different specific receptors against various antigens are present then altogether more antigen material would be bound compared to the presence of one specific receptor.

If several specific antigens are coupled to the solid phase, a mixture of receptors R2a, R2b etc. which each are able to bind a particular antigen, preferably at other epitopes than receptors R1a, R1b etc. must likewise be used as receptor R2 which carries the label. If the antigens have identical epitopes or epitopes which are closely related it is also possible in this case to use an antibody as R2 which simultaneously recognizes all antigens which are to be determined.

In the immunological test a microtitre plate is preferably used as the solid phase which is coated with receptor R1 in order to be able to simultaneously test different dilutions of the sample material in a test preparation. If receptor R1 is not directly bound to the solid phase but is only to be bound during the course of the test via a binding pair such as biotin/streptavidin, one partner of the binding pair is immobilized to the solid phase, in the case of biotin/streptavidin this is preferably streptavidin.

The method according to the present invention is further elucidated by the following examples:

EXAMPLE 1

Detection of micrometastases of epithelial tumours in bone marrow by means of a cytokeratin ELISA Preparation of bone marrow by fractional lysis Bone marrow is collected pre-operatively from the *Cristae iliacae posteriores* of the iliac crest using a puncture needle. 3–6 ml bone marrow is collected in heparinised syringes per needle insertion site. The bone marrow is stored at 4° C. For the lysis of erythrocytes, 1 ml bone marrow is incubated for 5 minutes at room temperature in 40 ml lysis buffer. The lysis buffer has the following composition:

89.9 g/l ammonium chloride
10.0 g/l KHCO₂
370 mg/l EDTA

The lysis buffer is sterile filtered before use.

After the incubation it is centrifuged for 5 minutes at 300 g and room temperature. The supernatant is discarded and the cell pellet is resuspended in 1 ml PBS. The cell count is determined in this suspension, the cell suspension is dispensed in aliquots and adjusted to $5 \times 10^6$ cells/aliquot. After a further centrifugation at 8000 g for 3 minutes in an Eppendorf centrifuge the supernatant is pipetted off and the cells in the pellet are resuspended in 30 μl 0.9 % NaCl solution. The nucleated cells were lysed by a 10 minute treatment with ultrasound and 220 μl 40 mM phosphate buffer pH 7.4 was added. After renewed centrifugation in order to remove the cell fragments, the supernatant is used in the cytokeratin 19 ELISA.

Cytokeratin 19 ELISA

The cytokeratin 19 ELISA was carried out in a similar manner to that described in WO 91/10139. The same reagents and monoclonal antibodies were used. It was possible to further increase the sensitivity of the test compared to the test described in WO 91/10139 by a stepwise test procedure and by addition of 12 g/l polyethylene glycol with a molecular weight of 40000 to the buffer. 100 µl of a solution of a biotinylated antibody Ks 19.1 in 40 mM phosphate buffer pH 7.4, containing PEG is pipetted into a microtitre plate which is coated with streptavidin and incubated for 60 minutes. After washing three times 100 µl bone marrow extract which had been prepared as previously described was added by pipette and incubated for 90 minutes at room temperature. Afterwards it is again washed three times. It is again incubated for 90 minutes after addition of 100 µl of a solution of a peroxidase-labelled monoclonal antibody BM19 in 40 mM phosphate buffer, pH 7.4 containing PEG. After washing three times it is incubated at room temperature with 100 µl of the enzyme-substrate solution ABTS$^R$ (100 mM phosphate-citrate buffer pH 5.0, 1.47 mM sodium perborate, 9.1 mM ABTS$^R$) and the absorbance is measured after 60 minutes at 405 nm as a measure of the analyte concentration.

In the model experiment the test achieved a detection sensitivity of up to 10 HT 29 cells (cells of a colon carcinoma cell line) in $5 \times 10^6$ leucocytes. HT 29 cells were admixed in increasing concentrations to 1 ml whole blood. Subsequently it was lysed according to the protocol described above and the cytokeratin concentration was determined.

The bone marrow samples of 99 carcinoma patients were examined in parallel with the cytokeratin 19 ELISA and using immunocytology (Schlimok et al., Eur. J. Cancer 27, 1461–1465, 1991). The results of both methods were in agreement in 64 (65%) cases, of these 41 patients were negative and 23 patients positive. In a further 13 patients with negative cytology result an increased cytokeratin content, i.e. more than 100 pg, was detected in the cytokeratin 19 ELISA. Only 22 patients with a positive cytology result were negative n the cytokeratin 19 ELISA. Application of the chi-square method yielded a significant agreement ($X^2 = 7.75$, $p > 0.01$) between the methods of detection.

In 34 of the 99 patients bone marrow was collected from two puncture sites. In this case 70% of the results of both methods with respect to the puncture sites (n=133) were in fact in agreement.

We claim:

1. A method of screening for micrometastases of ectodermal or entodermal tumors in blood or bone marrow mesenchymal tissue, comprising the steps of:
    a) collecting mesenchymal tissue cells,
    b) lysing said mesenchymal tissue cells by non-detergent lysis and
    c) detecting cytokeratins or fragments thereof immunologically in any resulting cell supernatant.

2. The method according to claim 1 wherein step b) involves fractional lysis of the cells.

3. The method according to claim 2 wherein said mesenchymal tissue cells are lysed by addition of ammonium chloride and then any remaining intact cells are separated and lysed by ultrasound.

4. The method according to claim 1, wherein step c) is carried out using an ELISA test.

5. The method according to claim 1, wherein said cytokeratin is cytokeratin 19 or fragments thereof.

6. The method according to claim 1, wherein step c) is sensitive enough to detect less than 1000 cells of ectodermal or entodermal origin among $5 \times 10^6$ mesenchymal tissue cells.

7. The method according to claim 6, wherein step c) is sensitive enough to detect less than 100 cells of ectodermal or entodermal origin among $5 \times 10^6$ mesenchymal tissue cells.

8. The method according to claim 1, wherein step c) uses a sandwich assay with at least two receptors $R_1$ and $R_2$ which specifically bind cytokeratins or fragments thereof.

9. The method according to claim 8, wherein the sensitivity of step c) is increased by using a receptor mixture which contains at least two different receptors $R_1$ and at least two different receptors $R_2$.

10. The method according to claim 10, wherein $R_1$ is bound to a solid phase.

11. A method of screening for micrometastases of ectodermal or entodermal tumors in blood or bone marrow mesenchymal tissue, comprising the steps of:
    a) collecting mesenchymal tissue cells,
    b) incubating the mesenchymal tissue cells in lysis buffer,
    c) separating out any intact cells,
    d) thereafter lysing said intact cells by non-detergent lysis,
    e) centrifuging said cells to remove cell fragments, and
    f) detecting cytokeratins or fragments thereof immunologically in any resulting cell supernatant.

12. A test kit for screening for micro metastases of ectodermal or entodermal tumors in blood or bone marrow mesenchymal tissue comprising the following components in separate containers:
    a) a first cell lysis reagent containing ammonium chloride for the lysis of erythrocytes,
    b) a second cell lysis reagent for the lysis of nucleated cells, and
    c) a reagent for the immunological detection of cytokeratins or fragments thereof.

13. The test kit according to claim 12, wherein said reagent for immunological detection contains receptors $R_1$ and $R_2$ as well as a solid phase to which $R_1$ is bound or can be bound.

* * * * *